United States Patent [19]

Sun et al.

[11] Patent Number: 6,164,299

[45] Date of Patent: Dec. 26, 2000

[54] ION EXTRACTION APPARATUS FOR SINGLE SIDE WAFERS

[75] Inventors: Peng Sun, Cupertino, Calif.; Marty Adams, St. Charles, Mo.

[73] Assignee: MEMC Electronic Materials, Inc., St. Peters, Mo.

[21] Appl. No.: 09/525,984

[22] Filed: Mar. 15, 2000

Related U.S. Application Data

[62] Division of application No. 09/191,715, Nov. 12, 1998.

[51] Int. Cl.$^7$ ........................................ B08B 13/00
[52] U.S. Cl. .......................................... 134/113; 73/863.84
[58] Field of Search ........................... 134/2, 3, 21, 26, 134/32, 34, 36, 113; 73/863.83, 863.84, 864.34

[56] References Cited

U.S. PATENT DOCUMENTS

| | | |
|---|---|---|
| 4,023,931 | 5/1977 | Wolfgram . |
| 4,599,187 | 7/1986 | Hey .......................................... 252/171 |
| 5,030,293 | 7/1991 | Rich et al. . |
| 5,275,667 | 1/1994 | Ganesan et al. ............................. 134/1 |
| 5,284,802 | 2/1994 | Muraoka et al. ......................... 437/225 |
| 5,733,378 | 3/1998 | Berbel . |
| 5,783,938 | 7/1998 | Munson et al. . |
| 5,922,606 | 7/1999 | Jenkins et al. . |

FOREIGN PATENT DOCUMENTS

| | | |
|---|---|---|
| 05283381 | 10/1993 | Japan . |
| 2316483 | 2/1998 | United Kingdom . |

OTHER PUBLICATIONS

Anal. Chemical, "Determination of Boron and Phosphorus in Borophosphosilicate Thin Films on Silicon Substrates by Capillary Electrophoresis", by R. A. Carpio, et al., vol. 64, Issue 18, pp. 2123–2129, Sep. 1992.

Journal of Chromatography A, "Application of Capillary Zone Electrophoresis with an Isatachophoretic Initial State to Determine Anionic Impurities on As–Polished Silicon Wafer Surfaces", by J. Boden, et al., No. 696, pp. 321–332, 1995.

Chromatographia, "Optimization of the Electrokinetic Sample Introduction in Capillary Electrophoresis for the Ultra Trace Determination of Anions on Silicon Wafer Surfaces", by T. Ehmann, et al., vol. 45, pp. 301–311, 1997.

MICRO 93 Microcontamination Conference Proceedings, "Determination of Anionic Impurities on Silicon Wafers by Microextraction Capillary Electrophoresis", by Tom Talasek, et al., pp. 773–782, Oct., 1993.

Article entitled "Demonstrating a contamination–free wafer surface extraction system for use with CE and IC", Micromagazine, Apr., 1999, p. 41 XP002132594; Peng Sun, et al.

*Primary Examiner*—Philip R. Coe
*Attorney, Agent, or Firm*—Senniger, Powers, Leavitt & Roedel

[57] ABSTRACT

An apparatus for extracting inorganic ionic contaminants from a front surface of a silicon wafer for chemical analysis. The apparatus includes a container adapted to receive the wafer and inhibit air circulation over the front surface of the wafer. The container has a support for holding the wafer in a generally level orientation with the front surface of the wafer facing upwardly, an inlet orifice for introducing a layer of extraction fluid to the front surface of the wafer, and a sampling device for taking a sample from the layer of extraction fluid on the front surface of the wafer. The layer of extraction fluid is deposited upon only the front surface of the wafer and held for a period of time so that contaminants on the front surface are extracted into the layer of fluid. The container inhibits air circulation over the front surface of the wafer to preclude introducing contaminants to the extraction fluid that cause a false measurement of contaminants on the wafer. A portion of the layer of fluid is collected by a sampling device for subsequent analysis.

8 Claims, 2 Drawing Sheets

ION EXTRACTION APPARATUS FOR SINGLE SIDE WAFERS

CROSS-REFERENCE TO RELATED APPLICATION

This application is a divisional of application Ser. No. 09/191,715, filed Nov. 12, 1998 pending.

BACKGROUND OF THE INVENTION

This invention relates generally to silicon wafer cleaning, and in particular to an apparatus for determining inorganic ionic contamination on a single surface of a wafer.

A substantial concern in the manufacture of silicon wafers for semiconductor chips is surface contamination. Impurities degrade wafer surfaces allowing a haze to form on the surfaces, and can cause corrosion of metallic components of semiconductor devices. Among the contaminants that have a detrimental impact on the quality and reliability of integrated circuit devices are inorganic anions such as chloride, sulfate, nitrate, and fluoride.

Accurate measurement of silicon wafer surface anion contamination is crucial to maintain quality control of the manufacturing process. Contamination levels must be monitored to ensure that products are of a quality necessary for production of integrated circuit devices. Typically, a small percentage of production wafers are randomly sampled for testing. If anion concentration exceeds an allowable level, wafer production may be halted until the contamination source(s) can be identified and eliminated.

Previous measurement methods have not allowed testing a single side of a silicon wafer. Single-side data is of primary importance since integrated circuit devices are typically mounted only on one side of the wafer, and only on that side is contamination a concern. One technique established in the art for detection of inorganic ionic contaminants on all surfaces of the wafer is to perform a water extraction, in which the wafer is immersed in pure water for a period of time to cause a transfer of anions (which are water-soluble) from the wafer surface to the water. The water is subsequently analyzed using an ultra trace analysis method such as ion chromatography (IC) or capillary electrophoresis (CE) to determine anion concentrations. This technique provides the average contamination level of the entire wafer, including both sides, but precludes measuring contamination on a single surface.

Further, previous measurement methods are subject to inaccuracy and non-reproducibility. Sampled wafers are exposed to contamination not only during the manufacturing process but also during the contamination measurement process. Airborne gas phase species in any open environment circulate past deionized water used in an extraction and contaminate it. Even class 1 cleanrooms contain airborne molecular species contaminants. When IC or CE test results indicate high levels of contamination, uncertainty arises as to whether the impurities originate in the manufacturing process or in the measurement process.

SUMMARY OF THE INVENTION

Among the several objects and features of the present invention may be noted the provision of an apparatus to extract inorganic ionic contaminants from a single side of a silicon wafer; the provision of such an apparatus which provides an accurate sample of ionic inorganic contaminants on a single side of the wafer; the provision of such an apparatus that minimizes contamination from airborne sources; and the provision of such an apparatus which is economical to use.

Briefly, apparatus of the present invention extracts inorganic ionic contaminants from a front surface of a silicon wafer. The apparatus comprises a container adapted to receive the wafer, and a sampling device for taking a sample from the layer of extraction fluid on the front surface of the wafer. The container has a support for holding the wafer in a generally level orientation with the front surface of the wafer facing upwardly. The container is further adapted to inhibit air circulation over the front surface of the wafer. The container has an inlet orifice for introducing the layer of extraction fluid to the front surface of the wafer.

Other objects and features of the present invention will be in part apparent and in part pointed out hereinafter.

BRIEF DESCRIPTION OF THE DRAWINGS

Corresponding reference characters indicate corresponding parts throughout the views of the drawings.

DETAILED DESCRIPTION OF THE PREFERRED EMBODIMENT

Figure 1:
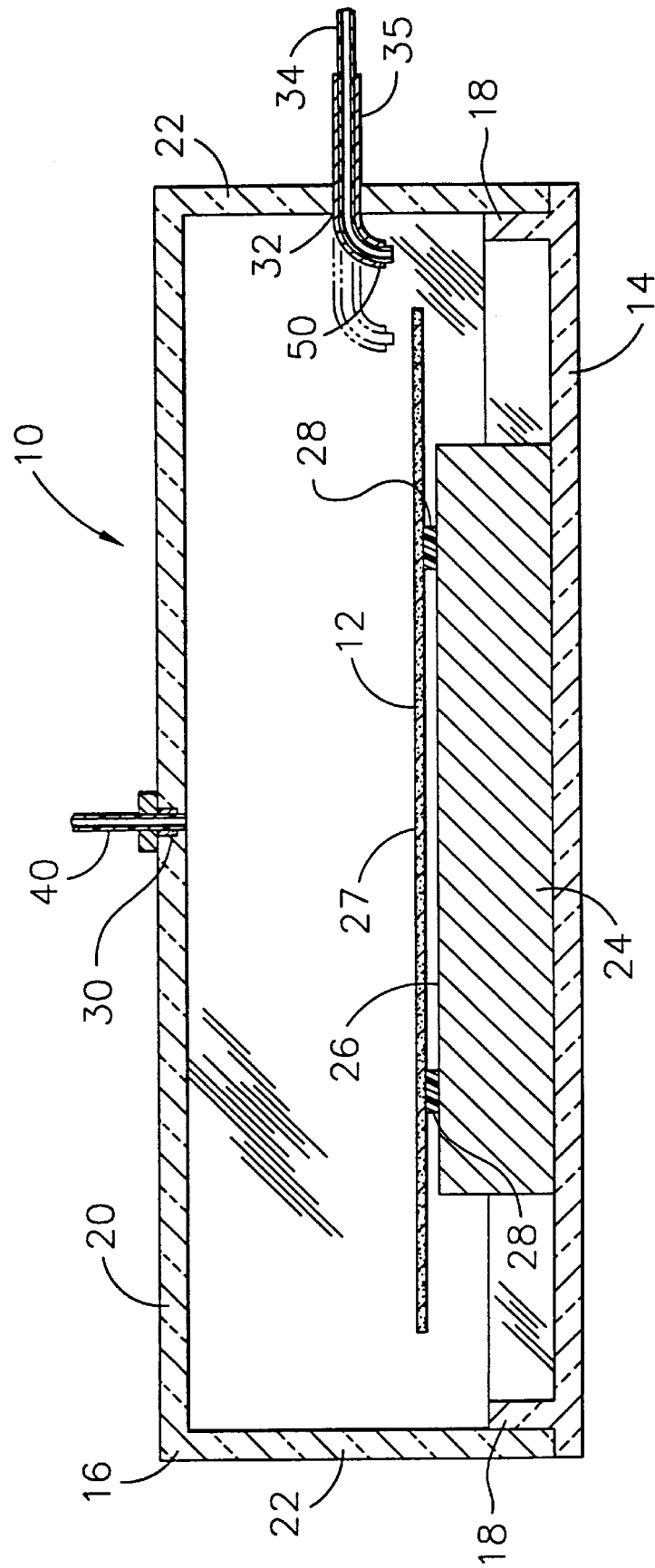
FIG. 1 is a cross-sectional view of a container of the present invention with a silicon wafer supported therein.

Referring now to the drawings and in particular to FIG. 1, a container for extracting inorganic ionic contaminants from a single side of silicon wafers is indicated generally at 10.

The container 10 is sized and shaped to enclose a single generally flat, thin wafer 12 such as those made of silicon in the manufacture of semiconductor chips for integrated circuit devices. The container 10 has an elongated rectangular shape, although cylindric or other shapes could work equally as well. The container 10 includes a generally flat bottom 14 for placement on a flat surface such as a table, and a cover 16. In the preferred embodiment, the bottom 14 and cover 16 are constructed of a suitable, uniform thickness, transparent material, such as polymethyl methacrylate (PLEXIGLASS).

The bottom 14 of the container 10 has a ridge 18 projecting upwardly from a position near an outer perimeter of the bottom. The ridge 18 extends in a closed geometric shape around the bottom 14, and is set back from an edge of the perimeter of the bottom a constant distance approximately equal to the thickness of the cover 16.

The cover 16 includes a top portion 20 and side walls 22. When placed over the bottom 14, the side walls 22 of the cover 16 engage the ridge 18 near the outer perimeter of the bottom, thereby to close the container 10. The engagement of the side walls 22 of the cover 16 against the ridge 18 of the bottom 14 forms a loose seal that prevents substantial air passage into or out of the container 10, thereby isolating the interior.

A platform 24 attached to the bottom 14 of the container 10 is substantially centered on the bottom. The platform 24 has a uniform height to provide a flat and level upper surface 26 of the platform at an elevation generally in the lower middle of the container. The upper surface 26 of the platform 24 has a plurality of support nubs 28 attached thereto. The wafer 12 rests on the support nubs 28. The platform 24 and support nubs 28 hold the wafer 12 in a generally level orientation with a front surface 27 of the wafer facing upwardly. In the preferred embodiment, there are four support nubs 28 glued to the upper surface 26 of the platform 24, each support nub being constructed of polyurethane.

Preferably, the container 10 is only as large as needed to receive the wafer 12 and permit the extraction operation to be carried out, as described more fully hereinafter. It is advantageous that the container 10 enclose no more volume of air than necessary, thereby minimizing exposure to airborne contaminants. Thus, differently sized containers are preferably used for wafers of different diameter. For extracting 300-mm diameter wafers, inner dimensions of the container 10 have been 355.6-mm×355.6-mm×76.2-mm, with a platform size of 177.8-mm×177.8-mm×25.4-mm. For 200-mm diameter wafers, container inner dimensions of 254-mm×254-mm×76.2-mm and a platform of 127-mm×127-mm×25.4-mm have been effective. The smaller dimension in all cases is the height.

The top portion 20 of the cover 16 of the container 10 has an inlet orifice 30 formed therein for introducing an extraction fluid into the container. The orifice 30 is located above the front surface 27 of the wafer 12 when supported on the platform 24. In the preferred embodiment, the orifice 30 is located near a center of the top portion 20.

An outlet orifice 32 is formed in one of the side walls 22 of the cover 16, as seen in FIG. 1, for removing fluid from the container 10. An outlet tube 34 extends through the outlet orifice 32 and is slidingly movable within it to facilitate fluid removal. A portion of the outlet tube 34 that extends through the outlet orifice 32 and toward the wafer 12 is wrapped in a sleeve tube 35. The outlet tube 34 is slidingly movable within sleeve tube 35, and the sleeve tube is slidingly movable within the outlet orifice 32. It is envisioned that the outlet orifice 32 may be located anywhere along the cover 16 or bottom 14 of the container 10, or may be combined with the inlet orifice 30, and still be within the scope of this invention.

Figure 2:
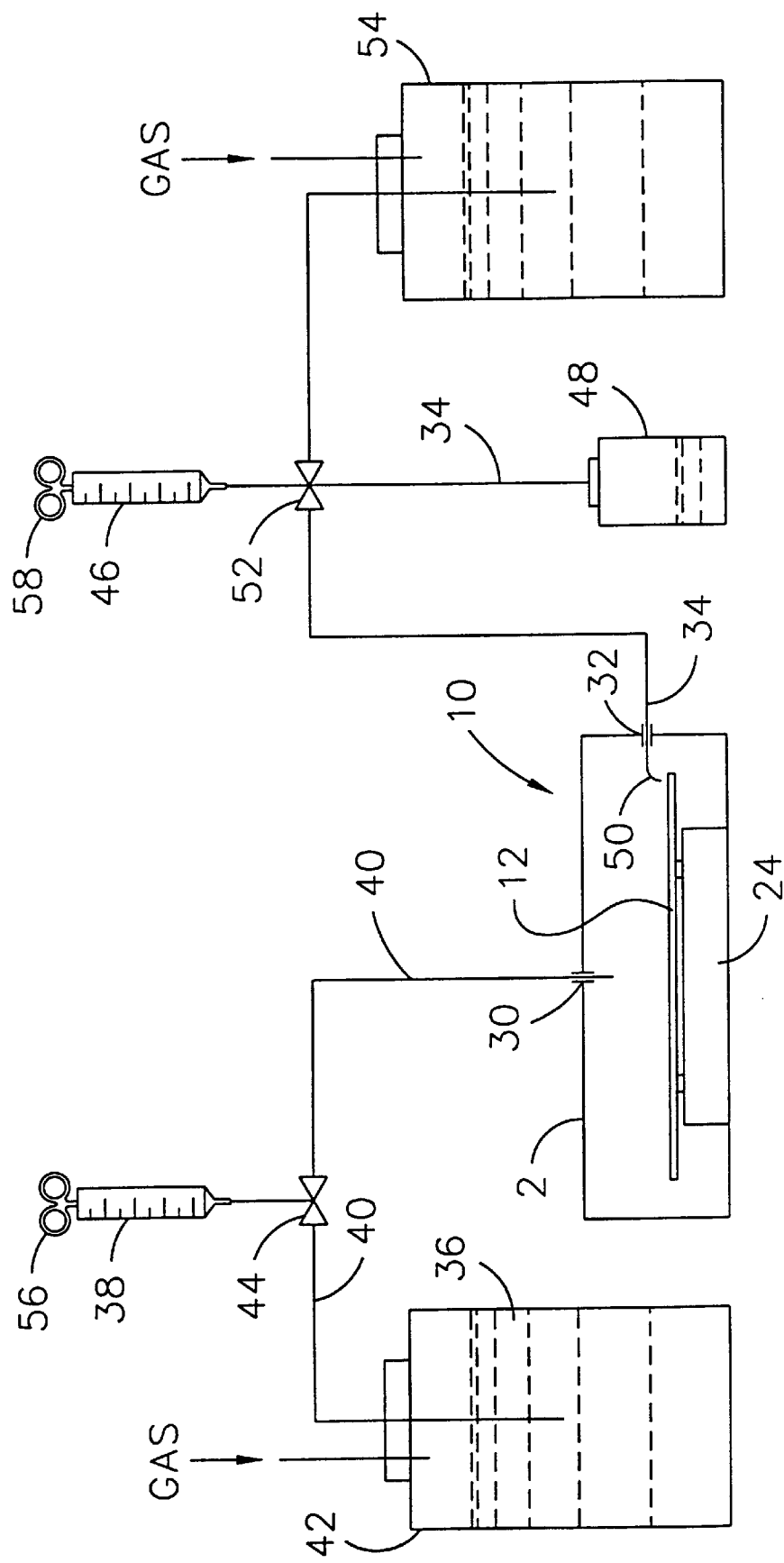
FIG. 2 is a schematic of an apparatus of the present invention including the container, two sources of fluid, two syringes, inlet tubing, outlet tubing, and a sample collection bottle.

Referring now to FIG. 2, the container 10 is shown in relation to other parts of the apparatus for performing the process of the present invention.

Means for introducing a layer of extraction fluid comprises a source of fluid 36, an injecting syringe 38, and inlet tubing 40 received through the inlet orifice 30. The source of fluid 36 is a first supply bottle 42 containing the extraction fluid and a gas. The gas fills an entire portion of the first supply bottle 42 that is not occupied by fluid, and it is pressurized to a level slightly greater than atmospheric pressure, such as 15 psi absolute. The pressurized gas prevents the entry of ambient air into the bottle, and facilitates removal of fluid from the bottle.

In the preferred embodiment, the extraction fluid is deionized water. Deionized water having a resistivity of 18 MΩ (Megohms) has been used with satisfactory results. The gas within the supply bottle 42 is Helium or Argon. The water and the gas are of high purity to ensure that no ionic inorganic contaminants are introduced to the water prior to extraction that would corrupt the test results.

Inlet tubing 40 adapted to convey fluid into the container 10 extends from the first supply bottle 42 to a first valve 44 and then to engagement with the inlet orifice 30 in the cover 16 of the container. The first valve 44 has a multi-port switching feature and is further connected by additional inlet tubing 40 to the first syringe 38. Preferably, the inlet tubing 40 is made of polytetrafluoroethylene (TEFLON).

A sampling device for taking a sample from the layer of extraction fluid includes the outlet tube 34, the sleeve tube 35, a sampling syringe 46, and a sample collection bottle 48. The outlet tube 34 has a curved sampling head 50 on a distal end. The sleeve tube 35 is of a thicker construction and more rigid than the outlet tube 34, and will more readily hold a shape. The sleeve tube 35 thereby helps the outlet tube 34, which is relatively flexible, to maintain a stiff and straight section through the outlet orifice 32 and to maintain the curved form of sampling head 50. Although the outlet tubing 34 is slidingly movable within the sleeve tube 35 for the necessary assembly of the apparatus, the tubing normally stays fixed relative to the sleeve tube in the process of the present invention. The outlet tube 34 and sleeve tube 35 are together slidingly movable in the outlet orifice 32 relative to the container 10, between a first position (shown in phantom in FIG. 1) in which an open end of the sampling head 50 is located over the front surface 27 of the wafer 12, and a second position (shown in solid lines in FIG. 1) in which the open end of the sampling head 50 is not over the front surface yet remains within the container. The outlet tubing 34 is preferably made of polytetrafluoroethylene (TEFLON), although other materials may be used without departing from the scope of the present invention.

The outlet tubing 34 extends from the sampling head 50 in the container to a second valve 52 and then to the sample collection bottle 48. The sample collection bottle 48 functions as a receptacle for the sample of fluid. The second valve 52 has a multi-port switching feature and is further connected by additional outlet tubing 34 to the sampling syringe 46 and to a second supply bottle 54. After an extraction process is complete, water from the second supply bottle 54 is provided for rinsing and purifying the apparatus, as hereinafter described. It is envisioned that one supply bottle could fulfill the purposes of both the first and second supply bottles, 42 and 54, respectively.

A process using apparatus of the present invention for extracting inorganic ionic contaminants from the front surface 27 of the silicon wafer 12 for chemical analysis begins by transferring the wafer from a conventional cassette (not shown) to the container 10. A conventional wafer transfer device (not shown) is used to place the wafer 12 upon the support nubs 28 of the platform 24. The front (i.e., finished) surface 27 of the wafer, the surface which is to be extracted, is generally level and faces upwardly.

The cover 16 of the container 10 is fitted on the bottom 14, so that the side walls 22 of the cover engage the ridge 18 near the outer perimeter of the bottom to close the container. Air circulation near the wafer 12 from the surrounding room is thereby inhibited, minimizing the quantity of airborne contaminants to which the wafer is exposed during the time of the extraction.

The layer of extraction fluid is next deposited upon the front surface 27 of the wafer 12. To do this, a plunger 56 of the injecting syringe 38 is extended to create a vacuum in the inlet tubing 40 and draw deionized water from the first supply bottle 42 through the inlet tubing and the first valve 44 into the injecting syringe. The first valve 44 is switched to shut a line of inlet tubing 40 from the first supply bottle 42 and open a line to the container 10. The plunger 56 of the injecting syringe 38 is compressed, forcing the water from the syringe through the first valve 44 and the inlet orifice 30 into the container 10. The water drops onto the front surface 27 of the wafer 12.

A quantity of fluid is deposited to create a thin layer, preferably covering all of the front surface 27. In practice, it has been found that for 300 mm diameter wafers, about 40 ml of fluid is effective; for 200 mm wafers, about 20 ml of fluid works well.

The layer of extraction fluid rests on the front surface 27 of the wafer 12 for a period of time to extract ion contaminants from the front surface to the fluid. The water soluble ions that contaminate the front surface 27 are dissolved into the water. Although a period of about 10 minutes has been successful, a period of about 15 minutes is preferable to ensure the effectiveness of the process. During that time period, it is advantageous to gently roll or shake the container 10 to agitate the layer of fluid. The agitation facilitates the transfer of ions from the front surface 27 to the fluid and makes the concentration of ions more uniform throughout the layer. Intermittent agitation has proven adequate, such as once every two to three minutes.

When the container 10 is gently shaken, the wafer 12 remains stationary relative to the container since the plurality of support nubs 28 provide adequate lateral frictional support to prevent the wafer from sliding on the platform 24. Further, the layer of extraction fluid continues to cover substantially all of the front surface 27 of the wafer 12. The fluid is rolled about and redistributed around the front surface 27, but surface tension keeps the fluid upon the front surface and prevents spillage. During extraction, the outlet tubing 34 is slid to the second position where the open end of the sampling head 50 remains away from the wafer 12.

After the time period for extraction is complete, the sampling head 50 is slidably moved to the first position so that the open end is closely adjacent the layer of fluid on the front surface 27 of the wafer 12. A portion of the layer of fluid from the front surface 27 is collected for subsequent analysis. A plunger 58 of the sampling syringe 46 is extended, creating a vacuum in the outlet tubing 34 and drawing fluid from the front surface 27 through the outlet tubing, the outlet orifice 32, and the second valve 52 into the sampling syringe. The container 10 may need to be tilted slightly to bias the layer of extraction fluid toward the open end of the sampling head 50 for efficient collection. Further, the outlet tubing 34 may need to be rotated, tilted, slid relative to sleeve tube 35, or otherwise manipulated to place the open end in a location for water collection. In practice, the open end of the sampling head 50 of outlet tube 34 often makes contact with the front surface 27 of the wafer 12.

After fluid has been drawn into the sampling syringe 46, the second valve 52 is switched to shut a line of outlet tubing 34 from the container 10 and open a line to the sample collection bottle 48. The plunger 58 of the sampling syringe 46 is compressed, forcing the fluid from the syringe through the second valve 52 into the sample collection bottle 48. In practice, the entire layer of fluid need not be collected, since only about 10 ml of fluid are needed for subsequent analysis.

The sample collection bottle 48 is removed and the extraction fluid is delivered for chemical analysis by a suitable ultra trace method such as conventional ion chromatography (IC) or capillary electrophoresis (CE). That analysis provides the average concentrations of $NH_4^+$, $Br^-$, $Cl^-$, $SO_4^{2-}$, $NO_3^-$, $F^-$, and $HPO_4^{2-}$ that were present on the front surface 27 of the wafer 12. The sampling head 50 is slid back to the second position, and the wafer 12 is removed from the container 10.

Pure water from the second supply bottle 54 is used to rinse and purify the outlet tubing 34, second valve 52, and sampling syringe 46 in preparation for an extraction of a new wafer. To do this, the second valve 52 is switched to open a line of tubing 34 from the second supply bottle 54. The plunger 58 of the sampling syringe 46 is extended, drawing pure water into the sampling syringe. The water absorbs residual contaminants within the interior of the sampling syringe 46. The plunger 58 is compressed, forcing water through the line of outlet tubing 34 that extends toward the sample collection bottle 48, thereby rinsing the interior of the second valve 52 and the tubing 34. The bottle 48 has been previously removed, so that the water flows out of the apparatus for suitable disposal.

The second valve 52 is switched to open the line of tubing 34 from the container 10. The plunger 58 of the sampling syringe 46 is further compressed forcing water toward the container 10, thereby rinsing the interiors of the second valve 52, the tubing 34, and the curved sampling head 50. The water flows into the bottom of the container 10 and is suitably removed. This rinse process ensures purification and precludes any carryover effect from one wafer extraction to another. The apparatus is then ready to be used again.

In view of the above, it will be seen that the several objects of the invention are achieved and other advantageous results obtained.

As various changes could be made in the above without departing from the scope of the invention, it is intended that all matter contained in the above description and shown in the accompanying drawings shall be interpreted as illustrative and not in a limiting sense.

What is claimed is:

1. An apparatus for extracting inorganic ionic contaminants from a front surface of a silicon wafer to an extraction fluid, the apparatus comprising:

a container adapted to receive the wafer, the container having a support for holding the wafer in a generally level orientation with the front surface of the wafer facing upwardly, the container being closeable whereby air passage into or out of the container is prevented to inhibit circulation of air in a surrounding room over the front surface of the wafer, the container having an inlet orifice for introducing a layer of the extraction fluid to the front surface of the wafer; and a sampling device for taking a sample from the layer of extraction fluid on the front surface of the wafer for subsequent chemical analysis.

2. The apparatus as set forth in claim 1 wherein the inlet orifice is located above the front surface of the wafer, and wherein the container has an outlet orifice formed therein for removing said sample of extraction fluid from the container.

3. The apparatus as set forth in claim 2 wherein the sampling device comprises an outlet tube extending through the outlet orifice in the container, the outlet tube being slidingly movable in the outlet orifice relative to the container between a first position in which a distal end of the outlet tube is located over the front surface, and a second position in which the distal end of the outlet tube is not over the front surface.

4. The apparatus as set forth in claim 3 wherein the sampling device further comprises a sampling syringe in selective fluid communication with the outlet tube and a sample collection bottle in selective fluid communication with the syringe.

5. The apparatus as set forth in claim 4 further comprising a source of the extraction fluid, an injecting syringe, and inlet tubing received through the inlet orifice to convey the extraction fluid into the is container.

6. The apparatus as set forth in claim 1 wherein said support for holding the wafer in a generally level orientation comprises a platform having a plurality of support nubs for supporting the wafer and resisting lateral motion of the wafer.

7. The apparatus as set forth in claim 1 wherein the container includes a cover and a bottom, the cover being engageable against the bottom to form a seal that inhibits air passage into or out of the container.

8. The apparatus as set forth in claim 7 wherein the bottom has an upwardly projecting ridge and the cover has side walls that engage the ridge.

* * * * *

UNITED STATES PATENT AND TRADEMARK OFFICE
CERTIFICATE OF CORRECTION

PATENT NO. : 6,164,299 Page 1 of 1
DATED : December 26, 2000
INVENTOR(S) : Peng Sun, Marty Adams It is certified that error appears in the above-identified patent and that said Letters Patent is hereby corrected as shown below:

Column 6, claim 5,
Line 54, "into the is container" should read -- into the container --.

Signed and Sealed this

Twenty-ninth Day of January, 2002

Attest:

*Attesting Officer*

JAMES E. ROGAN
*Director of the United States Patent and Trademark Office*